United States Patent
Ianchulev (10) Patent No.: US 9,445,890 B2
(45) Date of Patent: *Sep. 20, 2016

(54) INTRAOPERATIVE ESTIMATION OF INTRAOCULAR LENS POWER

(71) Applicant: WaveTec Vision Systems, Inc., Aliso Viejo, CA (US)

(72) Inventor: Tsontcho Ianchulev, Los Angeles, CA (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/098,447

(22) Filed: Dec. 5, 2013

(65) Prior Publication Data

US 2014/0249624 A1  Sep. 4, 2014

Related U.S. Application Data (60) Continuation of application No. 13/619,787, filed on Sep. 14, 2012, now Pat. No. 8,632,185, which is a continuation of application No. 12/581,061, filed on Oct. 16, 2009, now Pat. No. 8,313,196, which is a (Continued)

(51) Int. Cl.
*A61B 3/00* (2006.01)
*A61F 2/16* (2006.01)

(Continued)

(52) U.S. Cl.
CPC .............. *A61F 2/16* (2013.01); *A61B 3/0033* (2013.01); *A61B 3/103* (2013.01); *A61B 3/1015* (2013.01); *A61F 9/0017* (2013.01); *A61B 3/13* (2013.01)

(58) Field of Classification Search
CPC .... A61B 3/13; A61B 3/103; A61B 19/5223; G02B 21/0012
USPC ...... 351/246, 221, 208, 212; 623/6.11, 6.12; 606/27; 128/898

See application file for complete search history.

(56) References Cited

U.S. PATENT DOCUMENTS 4,019,813 A   4/1977 Cornsweet et al.
4,125,320 A   11/1978 Rassow (Continued)

FOREIGN PATENT DOCUMENTS

AU   2005234778   8/2011
CA   2515010      5/2013

(Continued)

OTHER PUBLICATIONS

Combined International Search Report and Written Opinion of the International Searching Authority for International Application No. PCT/US05/13550; issued by the ISA/US; dated Nov. 15. 2005.

(Continued)

*Primary Examiner* — Hung Dang
(74) *Attorney, Agent, or Firm* — Baker Botts L.L.P.

(57) ABSTRACT

Apparatus for performing intraocular implant surgery, including surgical apparatus for performing intraocular implant surgery, an autorefraction device associated with the surgical apparatus, wherein the autorefraction device is configured to perform autorefraction on the aphakic eye to provide one or more aphakic refraction measurements, and a processor connected to the autorefraction device, wherein the processor is configured to process the aphakic refraction measurements and provide the user of the apparatus with information regarding the power of the intraocular lens.

3 Claims, 2 Drawing Sheets

Related U.S. Application Data continuation of application No. 12/499,079, filed on Jul. 7, 2009, now Pat. No. 7,988,291, which is a division of application No. 10/820,635, filed on Apr. 8, 2004, now Pat. No. 7,556,378.

(60) Provisional application No. 60/461,429, filed on Apr. 10, 2003.

(51) Int. Cl.
| | | |
|---|---|---|
| *A61B 3/103* | (2006.01) | |
| *A61F 9/00* | (2006.01) | |
| *A61B 3/10* | (2006.01) | |
| *A61B 3/13* | (2006.01) | |

(56) References Cited

U.S. PATENT DOCUMENTS

| | | |
|---|---|---|
| 4,172,662 A | 10/1979 | Vogel |
| 4,173,398 A | 11/1979 | Okamoto et al. |
| 4,293,198 A | 10/1981 | Kohayakawa et al. |
| 4,353,625 A | 10/1982 | Nohda et al. |
| 4,372,655 A | 2/1983 | Matsumura et al. |
| 4,376,573 A | 3/1983 | Matsumura et al. |
| 4,390,255 A | 6/1983 | Nohda et al. |
| 4,421,391 A | 12/1983 | Matsumura et al. |
| 4,459,027 A | 7/1984 | Kafri et al. |
| 4,541,697 A | 9/1985 | Remijan |
| 4,640,596 A | 2/1987 | Humphrey |
| 4,650,301 A | 3/1987 | Humphrey |
| 4,669,835 A | 6/1987 | Humphrey |
| 4,692,003 A | 9/1987 | Adachi et al. |
| 4,710,193 A | 12/1987 | Volk |
| 4,721,379 A | 1/1988 | L'Esperance |
| 4,730,917 A | 3/1988 | Krueger |
| 4,911,711 A | 3/1990 | Telfair et al. |
| 4,964,715 A | 10/1990 | Richards |
| 4,984,883 A | 1/1991 | Winocur |
| 4,995,716 A | 2/1991 | Warnicki et al. |
| 5,080,477 A | 1/1992 | Adachi |
| 5,144,478 A | 9/1992 | Toshimitsu |
| 5,157,427 A | 10/1992 | Humphrey |
| 5,164,750 A | 11/1992 | Adachi |
| 5,206,672 A | 4/1993 | Rowe |
| 5,208,619 A | 5/1993 | Campbell |
| 5,223,863 A | 6/1993 | Heine |
| 5,252,999 A | 10/1993 | Sukigara |
| 5,258,791 A | 11/1993 | Penney et al. |
| 5,270,749 A | 12/1993 | Okumura |
| 5,282,852 A | 2/1994 | Capetan et al. |
| 5,294,971 A | 3/1994 | Braunecker et al. |
| 5,307,097 A | 4/1994 | Baker |
| 5,329,322 A | 7/1994 | Yancey |
| 5,374,193 A | 12/1994 | Trachtman |
| 5,450,143 A | 9/1995 | Rowe et al. |
| 5,455,645 A | 10/1995 | Berger et al. |
| 5,493,109 A | 2/1996 | Wei et al. |
| 5,576,780 A | 11/1996 | Yancey |
| 5,777,719 A | 7/1998 | Williams et al. |
| 5,796,463 A | 8/1998 | Bullimore |
| 5,800,533 A | 9/1998 | Eggleston et al. |
| 5,861,937 A | 1/1999 | Fujieda |
| 5,909,268 A | 6/1999 | Isogai et al. |
| 5,936,706 A | 8/1999 | Takagi |
| 5,949,521 A | 9/1999 | Williams et al. |
| 5,963,300 A | 10/1999 | Horwitz |
| 5,968,094 A | 10/1999 | Werblin et al. |
| 5,968,095 A | 10/1999 | Norrby |
| 5,994,687 A | 11/1999 | Chanteloup et al. |
| 6,002,484 A | 12/1999 | Rozema et al. |
| 6,004,313 A | 12/1999 | Shimmick et al. |
| 6,007,204 A | 12/1999 | Fahrenkrug et al. |
| 6,042,232 A | 3/2000 | Luce et al. |
| 6,043,885 A | 3/2000 | Mazuet et al. |
| 6,050,687 A | 4/2000 | Bille et al. |
| 6,086,204 A | 7/2000 | Magnante |
| 6,095,651 A | 8/2000 | Williams et al. |
| 6,096,077 A | 8/2000 | Callahan et al. |
| 6,155,684 A | 12/2000 | Bille et al. |
| 6,199,986 B1 | 3/2001 | Williams et al. |
| 6,251,101 B1 | 6/2001 | Glockler |
| 6,262,328 B1 | 7/2001 | Wicks et al. |
| 6,264,328 B1 | 7/2001 | Williams et al. |
| 6,270,221 B1 | 8/2001 | Liang et al. |
| 6,271,915 B1 | 8/2001 | Frey et al. |
| 6,275,718 B1 | 8/2001 | Lempert |
| 6,299,311 B1 | 10/2001 | Williams et al. |
| 6,299,618 B1 | 10/2001 | Sugiura |
| 6,338,559 B1 | 1/2002 | Williams et al. |
| 6,379,005 B1 | 4/2002 | Williams et al. |
| 6,382,793 B1 | 5/2002 | Lai et al. |
| 6,382,794 B1 | 5/2002 | Lai et al. |
| 6,382,795 B1 | 5/2002 | Lai |
| 6,394,605 B1 | 5/2002 | Campin et al. |
| 6,409,345 B1 | 6/2002 | Molebny et al. |
| 6,419,671 B1 | 7/2002 | Lemberg |
| 6,439,720 B1 | 8/2002 | Graves et al. |
| 6,460,997 B1 | 10/2002 | Frey et al. |
| 6,497,483 B2 | 12/2002 | Frey et al. |
| 6,508,812 B1 | 1/2003 | Williams et al. |
| 6,550,917 B1 | 4/2003 | Neal et al. |
| 6,561,648 B2 | 5/2003 | Thomas |
| 6,570,143 B1 | 5/2003 | Neil et al. |
| 6,572,230 B2 | 6/2003 | Levine |
| 6,575,572 B2 | 6/2003 | Lai et al. |
| 6,578,963 B2 | 6/2003 | Pettit |
| 6,585,723 B1 | 7/2003 | Sumiya |
| 6,588,902 B2 | 7/2003 | Isogai |
| 6,598,975 B2 | 7/2003 | Liang et al. |
| 6,601,956 B1 | 8/2003 | Jean et al. |
| 6,609,793 B2 | 8/2003 | Norrby et al. |
| 6,609,794 B2 | 8/2003 | Levine |
| 6,626,535 B2 | 9/2003 | Altmann |
| 6,626,538 B1 | 9/2003 | Arrowsmith |
| 6,634,751 B2 | 10/2003 | Turner et al. |
| 6,637,884 B2 | 10/2003 | Martino |
| 6,658,282 B1 | 12/2003 | Eagan et al. |
| 6,679,606 B2 | 1/2004 | Campin et al. |
| 6,685,319 B2 | 2/2004 | Watson et al. |
| 6,702,806 B2 | 3/2004 | Gray et al. |
| 6,705,729 B2 | 3/2004 | Piers et al. |
| 6,724,464 B2 | 4/2004 | Yang et al. |
| 6,736,509 B2 | 5/2004 | Martino et al. |
| 6,736,510 B1 | 5/2004 | Van Heugten |
| 6,739,721 B2 | 5/2004 | Altmann |
| 6,761,454 B2 | 7/2004 | Lai et al. |
| 6,781,681 B2 | 8/2004 | Horwitz |
| 6,786,603 B2 | 9/2004 | Altmann |
| 6,793,654 B2 | 9/2004 | Lemberg |
| 6,819,413 B2 | 11/2004 | Neal et al. |
| 6,827,444 B2 | 12/2004 | Williams et al. |
| 6,836,374 B2 | 12/2004 | Esch et al. |
| 6,905,641 B2 | 6/2005 | Platt et al. |
| 6,908,196 B2 | 6/2005 | Herekar et al. |
| 6,926,710 B2 | 8/2005 | Cox et al. |
| 6,948,818 B2 | 9/2005 | Williams et al. |
| 6,997,555 B2 | 2/2006 | Dick et al. |
| 7,018,376 B2 | 3/2006 | Webb |
| 7,034,949 B2 | 4/2006 | Horwitz |
| 7,044,602 B2 | 5/2006 | Chernyak |
| 7,044,604 B1 | 5/2006 | Arrowsmith |
| 7,057,806 B2 | 6/2006 | Atkinson |
| 7,066,928 B2 | 6/2006 | Dick et al. |
| 7,068,439 B2 | 6/2006 | Esch et al. |
| 7,070,276 B2 | 7/2006 | Koretz |
| 7,077,522 B2 | 7/2006 | Williams |
| 7,111,938 B2 | 9/2006 | Andino et al. |
| 7,182,780 B2 | 2/2007 | Terwee et al. |
| 7,237,898 B1 | 7/2007 | Hohla et al. |
| 7,255,442 B2 | 8/2007 | Bucourt et al. |
| 7,303,281 B2 | 12/2007 | Wakil et al. |
| 7,336,371 B1 | 2/2008 | Haidner et al. |
| 7,341,348 B2 | 3/2008 | Eagan |
| 7,350,920 B2 | 4/2008 | Levine |

(56) References Cited

U.S. PATENT DOCUMENTS

| | | | |
|---|---|---|---|
| 7,357,509 B2 | 4/2008 | Williams et al. |
| 7,377,641 B2 | 5/2008 | Piers et al. |
| 7,380,942 B2 | 6/2008 | Molebny et al. |
| 7,401,919 B2 | 7/2008 | Vogelsang et al. |
| 7,406,263 B2 | 7/2008 | Graves et al. |
| 7,416,305 B2 | 8/2008 | Williams et al. |
| 7,425,067 B2 | 9/2008 | Warden et al. |
| 7,441,901 B2 | 10/2008 | Liang |
| 7,445,335 B2 | 11/2008 | Su et al. |
| 7,448,752 B2 | 11/2008 | Levine |
| 7,455,407 B2 | 11/2008 | Neal et al. |
| 7,461,938 B2 | 12/2008 | Lai |
| 7,467,869 B2 | 12/2008 | Kahlen |
| 7,475,989 B2 | 1/2009 | Campbell et al. |
| 7,476,248 B2 | 1/2009 | Harris et al. |
| 7,478,908 B2 | 1/2009 | Lai et al. |
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 | 9/2009 | Van Heugten |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |
| 8,313,196 B2 * | 11/2012 | Ianchulev | 351/246 |
| 8,333,474 B2 | 12/2012 | Michaels et al. |
| 8,394,083 B2 | 3/2013 | Van Heugten et al. |
| 8,475,439 B2 | 7/2013 | Van Heugten et al. |
| 8,632,185 B2 * | 1/2014 | Ianchulev | 351/246 |
| 2001/0041884 A1 | 11/2001 | Frey et al. |
| 2002/0016629 A1 * | 2/2002 | Sandstedt et al. | 623/6.11 |
| 2002/0082629 A1 | 6/2002 | Cox et al. |
| 2002/0105617 A1 * | 8/2002 | Norrby et al. | 351/177 |
| 2002/0107567 A1 | 8/2002 | Terwee et al. |
| 2002/0118349 A1 | 8/2002 | Yang et al. |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli |
| 2005/0105044 A1 | 5/2005 | Warden et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2007/0115432 A1 | 5/2007 | Thibos |
| 2008/0231809 A1 | 9/2008 | Haigis |
| 2013/0021574 A1 | 1/2013 | Van Heugten |
| 2013/0070203 A1 | 3/2013 | Michaels |

FOREIGN PATENT DOCUMENTS

| | | |
|---|---|---|
| CN | 2010-80040737.6 | 6/2011 |
| DE | 43 10 561 A1 | 9/1994 |
| EP | 0931504 A1 | 7/1999 |
| EP | 2444021 | 4/2012 |
| EP | 2453822 | 5/2012 |
| EP | 2453823 | 5/2012 |
| EP | 1596710 | 1/2013 |
| GB | 1 209 451 | 10/1970 |
| IL | 138282 | 7/2004 |
| JP | 11-24434 | 5/1989 |
| JP | 9-122075 | 5/1997 |
| JP | 10-272100 | 10/1998 |
| JP | 2000-139996 | 5/2000 |
| JP | 2001-507258 A | 6/2001 |
| JP | 2001-314372 A | 11/2001 |
| JP | 2002-306418 A | 10/2002 |
| JP | 2003-509731 A | 3/2003 |
| JP | 2003-102689 A | 4/2003 |
| JP | 4972546 | 4/2012 |
| WO | WO 92/01417 | 2/1992 |
| WO | WO 96/22506 | 7/1996 |
| WO | WO 98/27863 | 7/1998 |
| WO | WO 01/06914 | 2/2001 |
| WO | WO 01/21061 A1 | 3/2001 |
| WO | WO 01/26591 A1 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 A1 | 6/2003 |
| WO | WO 03/102498 A1 | 12/2003 |
| WO | WO 2004/093663 A2 | 11/2004 |
| WO | WO 2005/057252 | 6/2005 |
| WO | WO 2006/081031 A2 | 8/2006 |
| WO | WO 2009/086059 | 7/2009 |

OTHER PUBLICATIONS

Restriction Requirement issued on Apr. 10, 2007 in U.S. Appl. No. 10/820,635, filed Apr. 8, 2004.

Response to Restriction Requirement filed on May 3, 2007, in U.S. Appl. No. 10/820,635, filed Apr. 8, 2004.

Non-Final Office Action issued on Jul. 11, 2007 in U.S. Appl. No. 10/820,635, filed Apr. 8, 2004.

Office Action Response filed on Jan. 11, 2008 U.S. Appl. No. 10/820,635, filed Apr. 8, 2004.

Final Office Action issued on Apr. 10, 2008 in U.S. Appl. No. 10/820,635, filed Apr. 8, 2004.

Office Action mailed May 30, 2008 in Chinese Patent Application 200580011803.6 filed Apr. 20, 2005.

Office Action Mailed May 15, 2009 in Japanese Patent Application 2001-511810 filed Jul. 27, 1999.

Office Action mailed May 22, 2009 in Chinese Patent Application 200580011803.6 filed Apr. 20, 2005.

Office Action mailed Jun. 2, 2009, issued in U.S. Appl. No. 11/110,653, filed Apr. 20, 2005.

Office Action mailed Jul. 7, 2009, in U.S. Appl. No. 11/110,968, filed Apr. 20, 2005.

Rejection Decision issued Aug. 14, 2009 in Chinese Patent Application No. 2004-80003472.7 filed Jan. 20, 2004.

Office Action issued on Sep. 10, 2010 in in U.S. Appl. No. 12/499,079, filed Jul. 7, 2009.

Office Action mailed Dec. 18, 2009 in Japanese Patent Application 2006-502878 filed Jan. 20, 2004.

Office Action mailed Dec. 25, 2009 in Chinese Patent Application 200580011803.6 filed Apr. 20, 2005.

Final Office Action mailed Dec. 1, 2010 in U.S. Appl. No. 11/110,653, filed Apr. 20, 2005.

Office Action mailed Feb. 9, 2010 in Japanese Patent Application 2001-511810 filed Jul. 27, 1999.

International Search Report and Written Opinion for International Application No. PCT/US2009/063651 mailed Mar. 9, 2010.

International Search Report and Written Opinion, issued Apr. 30, 2010 in related International Patent Application No. PCT/US08/81584, filed Oct. 29, 2008.

(56) References Cited

OTHER PUBLICATIONS

RCE and Amendment filed Jul. 30, 2010 in U.S. Appl. No. 11/110,653, filed Apr. 20, 2005.
Notice of Allowance issued Sep. 28, 2010 in U.S. Appl. No. 11/110,653, filed Apr. 20, 2005.
International Search Report and Written Opinion mailed Oct. 7, 2010 for International Application No. PCT/US2010/041242.
Final Office Action mailed Oct. 29, 2010 in U.S. Appl. No. 11/110,968, filed Apr. 20, 2005.
Office Action dated Nov. 2, 2010 in Japanese Application No. 2007-509613 (with English Translation).
Amendment filed on Mar. 9, 2011 in U.S. Appl. No. 12/499,079, filed Jul. 7, 2009.
Notice of Allowance issued on Mar. 22, 2011 in U.S. Appl. No. 12/499,079, filed Jul. 7, 2009.
Request for Continued Examination, Final Amendment and Summary of Interview, filed in corresponding U.S. Appl. No. 11/110,968, filed Apr. 29, 2011.
Response to Office Action filed in corresponding U.S. Appl. No. 12/581,061, filed Jun. 28, 2011.
Preliminary Amendment filed Jul. 19, 2011 in corresponding U.S. Appl. No. 13/021,594.
Final Office Action issued on Sep. 6, 2011 in corresponding U.S. Appl. No. 12/581,061.
Notification of Reasons for Refusal mailed in corresponding Japanese Patent Application No. JP 2007-509613 on Oct. 11, 2011.
Office Action issued in corresponding European Patent Application No. 05737636 on Oct. 27, 2011.
Office Action mailed on Jan. 25, 2012 in corresponding U.S. Appl. No. 13/021,594, filed Feb. 4, 2011.
Request for Continued Examination, Amendment and Terminal Disclaimer filed in connection with U.S. Appl. No. 12/581,061, filed Mar. 5, 2012.
Decision to Grant issued on Mar. 13, 2012 in connection with Japanese Patent Application No. 2007-509613.
Notice of Allowance issued on Mar. 20, 2011 in connection with U.S. Appl. No. 12/581,061, filed Mar. 5, 2012.
Extended Search Report issued on Mar. 26, 2012 in connection with European Patent Application No. 12151139.8.
Office Action issued on Mar. 26, 2012 in connection with European Application No. EP 05737636.
Response to Office Action filed on May 22, 2012 in corresponding U.S. Appl. No. 13/021,594.
Restriction Requirement issued on Jun. 8, 2012 in corresponding U.S. Appl. No. 12/835,665.
Office Action issued on Jun. 8, 2012 in connection with U.S. Appl. No. 12/740,753.
Response to Restriction Requirement filed on Jul. 6, 2012 in corresponding U.S. Appl. No. 12/835,665.
Notice of Allowance issued on Jul. 11, 2012 in corresponding U.S. Appl. No. 13/021,594.
Notice of Allowance issued on Aug. 6, 2012 in connection with corresponding U.S. Appl. No. 12/206,974, filed Sep. 9, 2008.
Preliminary Amendment filed on Sep. 14, 2012 in corresponding U.S. Appl. No. 13/750,080.
Notice of Allowance issued on Sep. 17, 2012 in corresponding Canadian Application No. CA 2,515,010.
Non-Final Office Action issued on Oct. 5, 2012 in U.S. Appl. No. 12/835,665.
Request for Continued Examination filed on Oct. 10, 2012 in corresponding U.S. Appl. No. 13/021,594.
Office Action issued on Oct. 26, 2012 in connection with corresponding U.S. Appl. No. 13/619,168.
Notice of Allowance issued on Oct. 30, 2012 in connection with corresponding U.S. Appl. No. 13/021,594.
Office Action issued on Nov. 5, 2012 in connection with corresponding U.S. Appl. No. 12/830,221.
Response to Office Action filed Dec. 10, 2012 in corresponding U.S. Appl. No. 12/740,753.
European Search Report issued Dec. 21, 2012 in corresponding European Application No. 10800338.
Extended Search Report issued on Jan. 8, 2013 in connection with European Patent Application No. 10800335.
Response to Office Action filed Jan. 25, 2013 in connection with related U.S. Appl. No. 12/581,074.
Response to Office Action filed Jan. 28, 2013 in connection with related U.S. Appl. No. 13/619,168.
Office Action issued on Feb. 12, 2013 in connection with related Canadian Patent Application No. 2,561,388.
Final Office Action, issued on Feb. 19, 2013, in corresponding U.S. Appl. No. 12/835,668.
Office Action issued on Feb. 25, 2013, in corresponding U.S. Appl. No. 12/740,753.
Terminal Disclaimer and Interview Summary submitted on Feb. 27, 2013 in corresponding U.S. Appl. No. 13/619,168.
Office Action issued on Apr. 4, 2013, in corresponding EP Application No. 12 151 139.8.
Request for Continued Examination and Response to Office Action filed Aug. 9, 2013 in corresponding U.S. Appl. No. 12/581,074.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations," http://doctor-hill.com/iol-mail/piggyback.html, accessed on Feb. 12, 2010.
Aramberri, "Intraocular lens power calculation after corneal infrastructure surgery: Double-K method," J Cataract Refract Surg 29:2063-2068 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "Power of the Pre-Pupillary Pseudoshakos," B.J.O. 56:332-37 (1972).
Binkhorst, "The Optical Design of the Intraocular Lens Implants," Opthalmic Surg 6(3):17-31 (1975).
Brandser R., "Accuracy of IOL calculation in cataract surgery", Acta Ophthalmol Scand. Apr. 1997; 75(2):162-5 (Abstract).
Chen et al., "Analysis of intraocular lens power calculation in post-radial keratotomy eyes," J Cataract Refract Surg 29:65-? (Jan. 2003).
Colenbrander, "Calculation of the Power of an Iris-Clip Lens for Distance Vision," Br. J. Ophthal. 57:735-40(1973).
Cordonnier, M., et al., "How accurate is the hand-held refractor Retinomax(R) in measuring cycloplegic refraction: a further evaluation", Strabismus. Sep. 1998;6(3):133-142 (Abstract).
Cua et al., Intraocular lens calculations in patients with corneal scarring and irregular astigmatism, J Cataract Refract Surg 29:1352-1357 (Jul. 2003).
Dalens H, Marcellier JJ, Moussiere L., "Use of the SRK (Sanders-Retzlaff-Kraft) regression formula in the preoperative calculation of the power of crystalline implants" (Abstract).
El-Baha SM, et al., "Intraoperative biometry for intraocular lens (IOL) power calculation at silicone oil removal", Eur J Ophthalmol. Aug.-Sep. 2003;13(7):622-6. (Abstract).
El-Defrawy S., et al. "Evaluation of a hand-held autorefraotor in children younger than 6", J Pediatr Ophthalmol Strabismus. ~ar-Apr. 1998;35(2):107-9 (Abstract).
Feiz, et al., "Intraocular Lens Power Calculation After Laser In Situ Keratomileusis for Myopia and Hyperopia—A Standard Approach," Cornea 20(8):792-797 (2001).
Feordorov et al., "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia. 2003;56(1):11-4 (Abstract).
Gernet, "IOL Calculation According to Garnet and the GOW 70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001)

(56) References Cited

OTHER PUBLICATIONS

Gimbel et al., "Accuracy and Predictability of Intraocular Lens Power Calculation After photorefractive keratectomy," J Cataract Refract Surg 26:1147-1151 (Apr. 2000).
Gupta, et al., *"Design and use of an infrared Pupilometer for real-time pupil mapping in response to incremental illumination levels,"* 2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/Article Standard/Article/detail/559856.
Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden Intraokularlinse" [Intraoperative retinoscopy for determining the refractive value of an implantable intraocular lens] Klin. Augenheilkd. vol. 210, No. 4, 1997, pp. 207-212
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," J. Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions. CLAO J. 1984, 10:326-31.
Holladay, JT, et al. "Calculating the Surgically Induced Refractive Change Following Ocular Surgery", J. Cataract Refract. Surg. 1992; 18:429-43.
Hunt et al., "Evaluation of the measurement of refractive error by the PowerRefractor: a remote, continuous and binocular measurement system of oculomotor function," Br. J. Opthalmol 87:1504-1508 (2003).
Ianchulev, "Method for Intraoperative Refractive IOL Calculation," Poster Presentation at Ophthalmology Conference (Apr. 2004).
Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536. Abstract.
Isenberg et al., "Use of the HARK Autorefractor in Children," American Journal of Ophthalmology 131(4):438-441 (2001).
Iuorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).
Ivanov MN, et al., "Formula for calculating the IOL focal power", Vestn Oftalmol. Jul.-Aug. 2003:119 (4):52-4 (Abstract).
Iwami S. et al., "Prediction of Postoperative refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and LASIK", Korean J Ophthalmol. Jun. 2002;16(1):26-31 (Abstract).
Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).

Liang, et al. "Aberrations and Retinal Image Quality of the Normal Human Eye", J. Optical Society of America, vol. 14, No. 11, Nov. 1997.
Liang, et al. "Comparison of Measurements of Refractive Errors Between the Hand-held Retinomax and On-table Autorefractors in Cyclopleged and Noncyclopleged Children," American Journal of Ophthalmology 136(6): 1120-1128 (Dec. 2003).
Lipatov DV., "Assessment of the efficiency of different formulae applied to calculating the optic power of an intraocular lens in trans-scleral fixation", Vestn Oftalmol, Nov.-Dec. 2003; 119(6):33-5 (Abstract).
MA, et al., "Simple method for accurate alignment in toric phakic and aphakic intraocular lens implantation," J Cataract Refract Surg, Technique, Oct. 2008, vol. 34, pp. 1631-1636.
Masket, et al., "Atlas of Cataract Surgery," Book cover in 1 page, Front Matter in 11 pages (Table of Contents in 3 pages), Chapter 19 pp. 147-158, Published by Martin Dunitz Ltd 1999, United Kingdom.
Moreno-Barriuso, et al., "Laser Ray Tracing Versus Hartmann-Shack Sensor for Measuring Optical Aberrations in the Human Eye", J. Optical Society of America, vol. 17, No. 6, Jun. 2000.
Nemeth et al., "Optical and ultrasound measurement of axial length and anterior chamber depth for intraocular lens power calculation," J Cataract Refract Surg 29:85-88 (Jan. 2003).
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001).
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Quiroga, et al., *"Fourier transform method for automatic processing of moire deflectograms,"* Jun. 1999, Society of Photo-Optical Instrumentation Engineers, pp. 974-982.
Raj et al., "Clinical evaluation of automated refractio in anterior chamber pseudophakia," British Journal of Ophthalmology 75:42-44 (1991).
Raj et al., "Objective autorefraction in posterior chamber pseudophakia," British Journal of Ophthalmology 74:731-733 (1990).
Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).
Retzlaff J., "A new intraocular lens calculation formula", J Am Intraocul Implant Soc. Apr. 1980 6(2):148-52. (Abstract).
Rubin A., et al., "Variation during autorefraction: influence of two different target types", Ophthalmic Physiol Opt. Jan. 1997;17(1):38-43 (Abstract).
Sanders et al., "Comparison of the SRK/T formula and other theoretical and regression formulas," J Cataract Refract Surg. 16:341-346 (May 1990).
Sanders et al., "Comparisons of the SRK™ formula and other second generation formulas," J Cataract Refract Surg 14;136-141 (Mar. 1988).
Senjo, et al., "Prediction of Postoperative Refraction Using Intraoperative Retinoscopy," Journal of Japanese Ophthalmological Society, 1999, vol. 103, No. 7, pp. 551-555, Abstract.
Siganos et al., "Autorefractometry after laser in situ keratomileusis," J Cataract Refract Surg 29:133-137 (Jan. 2003).
Supplemental Admendment filed Apr. 1, 2010 in U.S. Appl. No. 11/110,968, filed Apr. 20, 2005.
Supplementary European Search Report for Application No. 05737636.0, Dated Mar. 19, 2009.
Suto et al., "Adjusting intraocular lens power for sulcus fixation," J Cataract Refract Surg 29:1913-1917 (Oct. 2003).
Thall et al., "Linear Regression Software for Intraocular Lens Implant Power Calculation," American Journal of Ophthalmology 101:597-599 (May 1986).

(56) References Cited

OTHER PUBLICATIONS

Thijssen JM., "The emmetropic and the iselkonic implant lens: computer calculation of the refractive power and its accuracy", Ophthalmologica. 1975;171 (6):467-86 (Abstract).

Thompson et al., "A New Posterior Chamber Intraocular Lens Formula for Axial Myopes," Ophthalmology 91(5): 484-488 (May 1984).

Tromans et al., "Accuracy of intraocular lens power calculation in paediatic cataract surgery," Br J Ophthalmol 85:939-941 (2001).

Tseng, et al., "Calculating the optimal rotation of a misaligned toric intraocular lens," J Catactact Refract Surg, Laboratory Science, Oct. 2008, vol. 34, pp. 1767-1772.

Villada Jr., et al., "Comparative evaluation of the Allergan Humphrey 570 and Canon RK-I autorefractors: II, Objective autorefraction in pseudophakes", Eye. 1992;6(Pt 3):287-9 (Abstract).

Van Heugten, T., et al. "Validation of Novel Hartmann-Moire Wavefront Sensor with Large Dynamic Range", presented at Wavefront Congress, Feb. 17, 2008, available at http://www.wavefront-congress.org/info/listing_detail.asp?absID-12, last visited Feb. 28, 2008.

Walline JJ, "Repeatability and validity of astigmatism measurements", J Refract Surg. Jan.-Feb. 1999; 15(1):23-31 (Abstract).

Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.

Wood IC., "A review of autorefractors", Eye. 1987;1 (Pt 4):529-35 (Abstract).

Yalvac IS, et al., "Calculation of intraocular lens power with the SRK IIformula for axial high myopia" Eur J Ophthalmol. Oct.-Dec. 1996;6(4):375-8 (Abstract).

Zaldivar et al., "Intraocular lens power calculations in patients with extreme myopia," J Cataract Refract Surg 26:668-674 (May 2000).

Rosales et al., "Phakometry and lens tilt and decentration using a custom-developed Purkinje imaging apparatus: validation and measurements," Journal of the Optical Society of America, vol. 23, No. 3, Mar. 2006, pp. 509-520.

Castro et al., "Tilt and decentration of intraocular lenses in vivo from Purkinje and Scheimpflug imaging Validation study," J. Cataract Refract. Surg. 2007; 33:418-429.

Tabernero et al., "Instrument for measuring the misalignments of ocular surfaces," Optical Society of America, Oct. 30, 2006, vol. 14, No. 22.

Uozato et al., "Intraoperative Confirmation Device for IOL Centering," Folia Ophthalmologica Japonica, vol. 41, 1990, pp. 1325-1329.

\* cited by examiner

INTRAOPERATIVE ESTIMATION OF INTRAOCULAR LENS POWER

CROSS-REFERENCE TO RELATED APPLICATIONS

This application is a continuation application of and claims priority to U.S. application Ser. No. 12/499,079, filed on Jul. 7, 2009, now U.S. Pat. No. 7,988,291 which application is a divisional application of and claims priority to U.S. application Ser. No. 10/820,635, filed on Apr. 8, 2004, now U.S. Pat. No. 7,556,378. This application also claims priority to U.S. Provisional Application Ser. No. 60/461,429, filed on Apr. 10, 2003. The disclosures of the prior applications are considered part of (and are incorporated by reference in) the disclosure of this 10 application.

TECHNICAL FIELD

This invention relates to methods and apparatus for selecting the power of an intraocular lens to be implanted into an eye.

BACKGROUND

The history of intraocular lens implantation dates back to 1949 when an initial attempt to replace a diseased lens with an artificial one resulted in a poor outcome with an error of −24.0 diopter (D). Nevertheless, this set the stage for continuous advances in the field of ophthalmology, leading to the common practice of "standard-of-care" lens implantation we see today. The technology of cataract surgery has witnessed an impressive development through constant innovation of surgical technique and instrumentation, lens material and design, and just as importantly, ever improving methodology for calculating and predicting the power of the lens implant necessary to achieve desired postoperative refractive outcome. In the 1960s Fyodorov was the first scientist to publish a formula for predicting the power of the intraocular lenses (IDLs) based on geometrical optics incorporating two very important preoperative anatomical parameters of the ocular system. *A-scan derived axial length of the eye and keratometry measurement of the cornea*, Feodorov S N, Kolinko A L. *Estimation of optical power of the intraocular lens*. Vestn. Oftamol; 80(4):27-31 (1967). Colenbrander published the first formula written in English in 1973. Colenbrander, *Calculation of the Power of an Iris-Clip Lens for Distance Vision*, Br. J. Ophthal. 57:735-40 (1973). Many further improvements followed these pioneering efforts. Binkhorst described a derivative formula in the 1970s. Binkhorst R D., *The optical design of intraocular lens implants*, Ophthalmic Surg 1975; 6(3):17-31. Binkhorst, *Power of the Pre-pupillary Pseudoshakos*, B.J.O. 56:332-37, (1972)). Modifications of the Colenbrander formula were implemented by Dr. Hoffer with further improvement of accuracy across the different axial length ranges. Hoffer K J. *Mathematics and computers in intraocular lens calculation*, Am Intra-Ocular Implant Soc J 1975; 1(1):4-5). In 1980, Sanders, Retzlaff and Kraff derived a regression formula which has sustained many subsequent updates and modifications. Further refinements were achieved with the second generation formulas which had better precision over a wider range of anatomic parameters, but all used axial length and corneal curvature (keratometry) as the main predictive variable in their models. Sanders, J. Retzlaff & M. C. Kraff, *Comparison of the SRK II Formula and the Other Second generation Formulas.*, J. Cataract & Refractive Surg. 14(3):136-41 (1988). Olsen, T., *Theoretical Approach to IOL Calculations Using Gaussian Optics*, J. Cataract & Refractive Surg. 13:141-45 (1987). Holladay, T. C. Praeger, T. Y. Chandler & K. H. Musgrove, *A Three-Party System for Refining Intraocular Lens Power Calculations*, J. Cataract & Refractive Surg. 14:17-24 (1988). J. T. Thompson, A. E. Maumenee & C. C. Baker, *A New Posterior Chamber Intraocular Lens Formula for Axial Myopes*, Ophthal. 91:484-88 (1984). Various improvements in making preoperative anatomic-based estimates of IOL power have been described in the patent literature (e.g., U.S. Pat. Nos. 6,634,751, 5,968,095, and 5,282,852).

The shortcomings of current technology are multifold. Even in the ideal and most simplified clinical setting, about 10-20% of patients remain with at least 1.0 diopter refractive error after surgery. In about 3-5% of cases this residual can be as high as 2 diopters. Also, traditional IOL estimation techniques based on axial length and corneal curvature produce even greater inaccuracy when the cataract surgery is done after vision correcting refractive surgery (e.g., Lasik, Lasek, wavefront and other similar corrective procedures). In this setting, a larger residual error can result (e.g., more than about 80% of such cases have about 1-1.5 diopter error). Reliance on anatomic measurements is even more problematic for a patient whose eye shape is at the extreme end of the range of an anatomic parameter.

Autoretinoscopy has been traditionally used for determination of the optical state of the ocular system in an office visit. In this office setting, autoretinoscopy is used as an objective measurement to guide the subjective testing and estimation of the power for corrective eye glass prescription. In this setting, an autorefractor based on the principle of automated retinoscopy, is used with the eye in the phakic state (i.e., with the native lens in its native position). A number of widely available autoretinoscopes are employed with the patient in a sitting position in front of the apparatus.

In recent years, very significant advances have been made in IOL surgical techniques and instrumentation (e.g., microincision techniques for quick and controlled cataract surgery), but IOL power has continued to be estimated preoperatively using anatomic measurements.

SUMMARY

The problems associated with current methods for IOL power estimation lie in the reliance on preoperative measurements, e.g., corneal curvature and axial length. These parameters can change significantly after the eye has been manipulated. For example, the curvature of the cornea and its optical properties change after incisions and intraocular procedures. Current models extrapolate the effective lens position of the implant through lens-associated constants, such as the A-constant, which are inherent to the specific lens design, but not to the particular anatomy of each eye, and therefore not individually customized to each surgical case. The current methods, because they only approximate the optical deficiency of the eye after lens extraction, lead to residual errors in lens power.

In a first aspect, the invention features a method for selecting the power of an intraocular lens, comprising extracting the native lens, performing autorefraction on the aphakic eye to provide one or more aphakic refraction measurements, and determining the power of the intraocular lens from the one or more aphakic refraction measurements.

Preferred implementations of this aspect of the invention may incorporate one or more of the following. The autorefraction may be performed with the patient in the same position in which the native lens was extracted. The position of the patient may be the supine position. The method may be used for patients that have previously undergone vision correcting refractive surgery. Determining the power of the intraocular lens may comprise using a predictive model that is an empirically derived relationship between the autorefraction measurements and the power of the intraocular lens. Determining the power of the intraocular lens may comprise using a predictive model that is a theoretically derived relationship between the autorefraction measurements and the power of the intraocular lens. The native lens may be extracted using a surgical microscope and the autorefraction may be performed using an autorefraction device configured to be moved into place for making autorefraction measurements following extraction of the native lens using the surgical microscope. The autorefraction may comprise making a plurality of autorefraction measurements and averaging the measurements. Determining the power of the intraocular lens may comprise determining the power from the one or more autorefractive measurements and from other parameters. The other parameters may include preoperative anatomic measurements of the eye. They may also include one or more of the following: intraocular pressure, intraoperative axial length, intraoperative keratometry, preoperative keratometry, preoperative axial length, intraoperative anterior chamber depth, or preoperative anterior chamber depth.

In a second aspect, the invention features apparatus for performing intraocular implant surgery, comprising surgical apparatus for performing intraocular implant surgery, an autorefraction device associated with the surgical apparatus, wherein the autorefraction device is configured to perform autorefraction on the aphakic eye to provide one or more aphakic refraction measurements, and a processor connected to the autorefraction device, wherein the processor is configured to process the aphakic refraction measurements and provide the user of the apparatus with information regarding the power of the intraocular lens.

Preferred implementations of this aspect of the invention may incorporate one or more of the following. The apparatus may further comprise a display for providing the user of the apparatus with the information regarding the power of the intraocular lens. The autorefraction device may be attached to or integrated with the surgical apparatus. The surgical apparatus may be a surgical microscope and the autorefraction device may comprise an autorefraction device configured to be moved into place for making refraction measurements following extraction of the native lens using the surgical microscope. The autorefraction device may be a portable autorefraction device that is used while a patient is in the supine position following surgical extraction of the lens. The autorefraction device may comprise a retinoscope. The autorefraction device may comprise a wavefront-based autorefraction device. The autorefraction device may comprise apparatus for measuring the aphakic dioptric state, the deficiency of the ocular system, or both the aphakic dioptric state and the deficiency of the ocular system. The autorefraction device may comprise or work in combination with an external lens, contact lens, intraocular lens, or other component with refractive or medium properties positioned along the optical axis along an autorefraction measurement trajectory. The surgical apparatus may comprise a surgical microscope that includes an ocular piece or display for centration and positioning and a toggle for XYZ movement, and wherein the autorefraction device may be positioned and configured so that movement of the toggle can adjust the position of the autorefraction device relative to the eye.

Among the many advantages of the invention (some of which may be achieved only in some of its various aspects and implementations) are the following: Greater precision is possible in estimating required IOL power, and thus there is less residual refractive error. It is possible to achieve reductions in the complexity and cost associated with IOL implantation surgery (e.g., it may be possible to eliminate the need for expensive equipment such as an A-scan biometry device and a keratometer, as well as the need for a separate pre-operative patient visit at which pre-operative eye measurements are made). The invention makes it possible to break away from the conventional preoperative anatomical approaches derived from Feodorov's original work in 1967. New refractive measurement technology can be used to predict the power of the intraocular lens. Anatomic parameters such as preoperative axial length and keratometry are no longer essential to the process of estimating the power of the intraocular lens (but these parameters, as well as others, may, in some implementations, be used in combination with the intraoperative autorefraction measurements). Relying on intraoperative measurement of the aphakic refractive state of the eye after lens extraction has the advantage that it measures the optical deficiency of the ocular system without the confounding interference of the native lens. Modern retinoscopy technology can be adapted to cataract surgery immediately after extraction of the cataract, when the eye is transiently aphakic; in this state, the cornea is the primary refractive medium and the optical system of the eye is in a unique state of non-interference by the lenticular optical component. When an autorefraction or other form of retinoscopy is done before a lens is implanted, the measurements are primed to correlate closely with the missing intraocular lens power. From these measurements the surgeon one can derive, correlate and calculate the parameters of the lens to be inserted. The method can be used solely for the purposes described or in combination with other ocular measurements and parameters obtained prior or during surgery to optimize accuracy and precision.

Other features and advantages of the invention will be found in the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
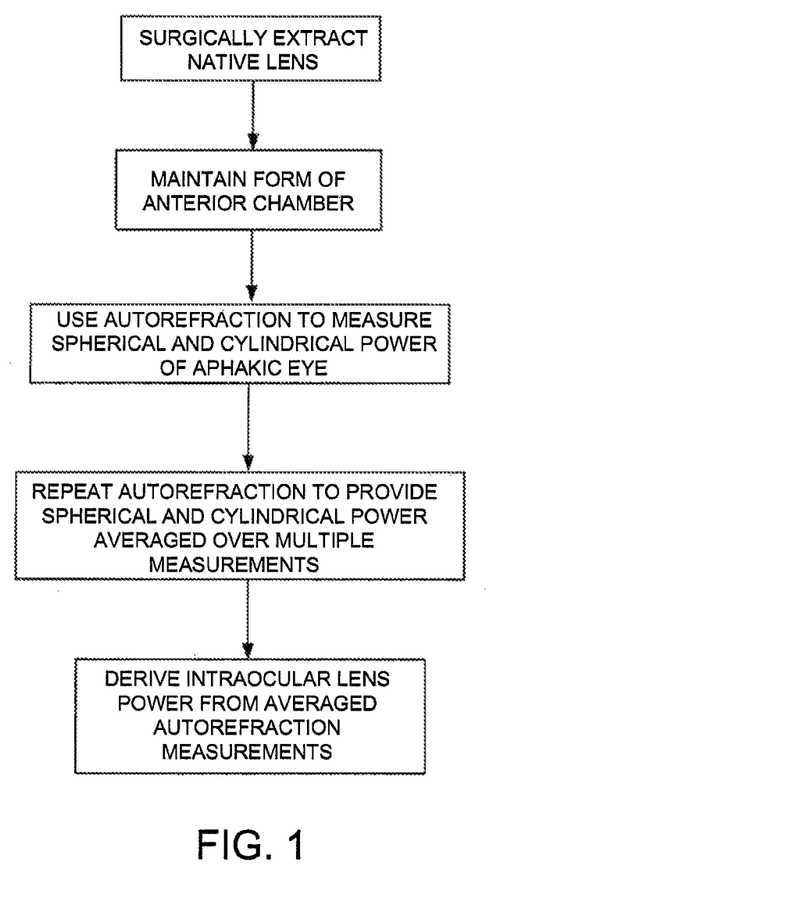
FIG. 1 is flow chart of steps in one implementation of the invention.

FIG. 1 shows the process followed in one implementation of the invention. Any surgical technique for lens extraction may be used, including such conventional techniques as phacoemulsification or extracapsular cataract extraction. After the lens is extracted from the eye and all particulate lens material is removed, the anterior chamber is maintained formed with intraocular fluid or viscoelastic. The eye is then centered and an autorefracting device is used to obtain a refractive reading of the aphakic eye (i.e., the eye with the lens removed). While any autorefractor can be used across a wide range of possible vertex distances, one possible implementation is to use an autorefractor with a vertex distance of 13.75 mm, and to take an average of multiple autorefraction measurements. Autorefraction provides a spherical and a cylindrical power measurement.

The power of the intraocular lens can be derived from the refraction measurements. One possible method for deriving the intraocular lens power is to use an empirically derived relationship, which could be called a predictive IOL model, that relates the refraction measurements to the IOL power. This can be done, for example, by first calculating the aphakic spherical equivalent of the refraction measurements from the standard formula:

Spherical Equiv=Measured Spherical Power+½ Measured Cylindrical Power, wherein Spherical Equiv is the aphakic spherical equivalent, Measured Spherical Power is the average of the spherical power measurements made using autorefraction, and Measured Cylindrical Power is the average of the cylindrical power measurements made using autorefraction. Next, the following empirically derived relationship may be used to relate the aphakic spherical equivalent to the IOL power:

IOL Power=$A$+$c$+$b$*(Spherical Equiv), wherein A is the lens specific constant (and depends on the type of intraocular lens being implanted), c is an empirically derived constant, and b is the empirically derived linear correlation coefficient.

The two empirically derived coefficients c, b may be derived using a statistical regression analysis of data relating IOL power to autorefraction measurement of the spherical equivalent. For example, the regression analysis may be performed on data collected from a large population of patients (e.g., one hundred patients). For each patient, the data comprise the IOL Power selected using conventional preoperative measurements and the spherical equivalent from an intraoperative autorefraction.

Other relationships between the refraction measurements and the IOL power may also be used, and the necessary constants and coefficients derived either empirically or theoretically. One alternative, of course, is to simply combine the two formulas as follows:

IOL Power=$A$+$c$+$b$*(Measured Spherical Power+½ Measured Cylindrical Power),

Varying the vertex distance of autorefraction or modifying the optical media along the optical path (e.g., by inserting a different material into the anterior chamber of the eye, or by placing a temporary lens in or near the eye) can alter the parametric variables of the relationship.

In some implementations, the above formulation can be improved with additional variables to achieve better precision. Parameters such as intraocular pressure, intraoperative axial length, intraoperative keratometry, preoperative keratometry, preoperative axial length, intra and preoperative anterior chamber depth can be used as supplementary correlates in the predictive model, in order to refine the IOL power. For example, the following relationship could be used:

IOL Power=$A$+$c$+$b$*(Spherical Equiv)+$d$*(Axial Length)+$f$*(Average Keratometry)+$g$*(Intraoperative Pressure)

In one implementation, both the surgery and the autorefraction are performed using standard available equipment. A standard surgical microscope is used for extraction of the native lens, and a standard portable autorefraction device (e.g., a Nikon Retinomax) is used for autorefraction. Both procedures may be performed while the patient remains in the same supine position. The refraction measurements are read from the autorefraction device, and the IOL power is calculated using a formula such as one of those given above.

Figure 2:
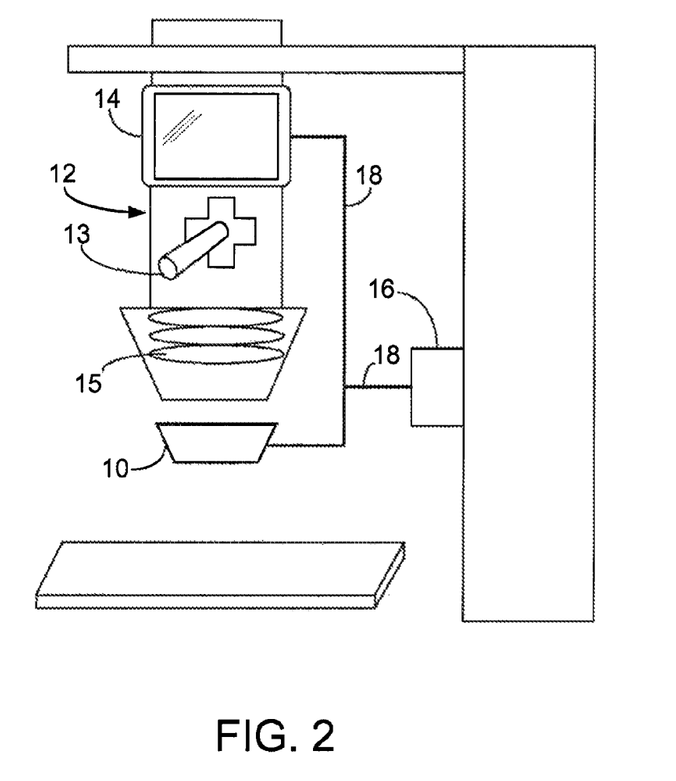
FIG. 2 is a diagrammatic view of apparatus implementing the invention in pone possible manner.

FIG. 2 shows another possible implementation in which specially designed equipment is used. An autorefraction retinoscope unit 10 is attached to the exterior of an ophthalmic surgical microscope 12. The surgical microscope in this implementation has its own display for centration and visualization. A toggle control 13 (and/or a pedal control) is provided for XYZ centration of the microscope and the retinoscope unit. The microscope has the usual lens array 15. The autorefraction unit can be a conventional automated retinoscopic apparatus of the type conventionally used to measure the dioptric deficiency and optical state of the phakic eye. The retinoscopic apparatus would be configured to operate with the patient in the supine position, intraoperatively, and to be moved out of the way of the microscopic surgical device when not in use, but configured so that its position and orientation is adjustable using the toggle control 13. A display unit 14 is integrated with the autorefraction unit 10 and also attached to the surgical microscope 12. The display unit presents the results of the IOL power determination. A processing unit 16 is electrically connected to the autorefraction unit and the display. Cables 18 make the electrical connections between the autorefraction unit 10, display unit 14, and processing unit 16. The processing unit receives measurement data from the autorefraction unit, and uses a predictive model (e.g., one of those described by the above formulas) to calculate the IOL power for display on the display unit.

An alternative to the arrangement shown in FIG. 2 would be to have the autorefraction unit, display unit, and processing unit fully integrated into the ophthalmic surgical microscope. For example, the same display unit can serve both for centration and visualization during surgery and for controlling and displaying results from the autorefraction unit and processing unit during IOL power determination.

The equipment of FIG. 2 or alternative implementations may be used to perform the eye surgery, to make the intraoperative refraction measurement, and to calculate the IOL power for achieving the desired emmetropia or postoperative refraction.

Many other implementations of the invention other than those described above are within the invention, which is defined by the following claims. For example, as earlier noted, completely separate surgical and autorefraction equipment may be used (e.g., with the microscope moved away, and the autorefraction equipment moved into place), and the IOL measurement may be calculated from the refraction measurements without using a special processor or display unit. Autorefraction may also be used after the intraocular lens is implanted (pseudophakic eye), to confirm whether a satisfactory choice has been made for the IOL power. If the autorefraction shows a residual error, the surgeon could immediately remove the implanted lens, and substitute another. Various types of autorefraction may be used to make the intraoperative refraction measurement of the aphakic eye.

The invention claimed is:

1. An ophthalmic method comprising:
   using an instrument that is associated with a surgical microscope to intraoperatively measure one or more optical properties of an eye from which the natural lens has been removed; and selecting an artificial lens to be inserted into the eye at least partially using the one or more measured optical properties.

2. An ophthalmic method comprising:

intraoperatively measuring one or more optical properties of an eye into which an artificial intraocular lens has been inserted; and determining a residual refractive error of the eye at least partially using the one or more measured optical properties in order to facilitate an intraoperative corrective action to reduce the residual refractive error.

3. An ophthalmic apparatus comprising:

a measurement device configured to be associated with a surgical microscope, wherein the measurement device is configured to intraoperatively measure one or more optical properties of an aphakic or pseudophakic eye; and a processor communicatively coupled to the measurement device, wherein the processor is configured to process the one or more measured optical properties and to provide a user with information for selection of an intraocular lens to be implanted into the eye or with information regarding an intraoperative corrective action to reduce residual refractive error.

* * * * *